United States Patent
Kumar et al.

(10) Patent No.: US 7,175,746 B2
(45) Date of Patent: Feb. 13, 2007

(54) POLYMER BASED ENZYME ELECTRODE FOR ESTIMATION OF CHOLESTEROL AND PROCESS FOR PREPARATION THEREOF

(75) Inventors: Arun Kumar, New Delhi (IN); Asha Chaubey, New Delhi (IN); Bansi Daar Malhotra, New Delhi (IN); Rajesh, New Delhi (IN); Surinder Krishan Grover, Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 444 days.

(21) Appl. No.: 10/277,089

(22) Filed: Oct. 22, 2002

(65) Prior Publication Data

US 2004/0074772 A1   Apr. 22, 2004

(51) Int. Cl.
 *G01N 27/327* (2006.01)
 *C25D 11/00* (2006.01)

(52) U.S. Cl. .......................... 204/403.14; 204/403.04; 205/317

(58) Field of Classification Search ............... 204/415, 204/317, 403.01–403.15; 435/11, 14, 25, 435/817; 205/317
 See application file for complete search history.

(56) References Cited

U.S. PATENT DOCUMENTS

| | | | | |
|---|---|---|---|---|
| 4,820,399 A | * | 4/1989 | Senda et al. ............ | 204/403.09 |
| 4,897,173 A | * | 1/1990 | Nankai et al. ......... | 204/403.05 |
| 5,575,895 A | * | 11/1996 | Ikeda et al. ............. | 204/403.1 |
| 5,695,947 A | * | 12/1997 | Guo et al. .................... | 435/11 |
| 5,795,953 A | * | 8/1998 | Kim et al. ................. | 526/258 |

OTHER PUBLICATIONS

Ramanathan, K. et al., "Dielectric Spectroscopic Studies on Polypyrrole Glucose Oxidase Films," Journal of Applied Polymer Science, 1996, vol. 60, Issue 13, pp. 2309-2316.*

Dall'Antonia, L. H. et al., "Amperometric Urea Biosensor Using Polypyrrole with Different Dopants," Electrochemistry Society Proceedings, 2001, vol. 2001-18 (Chemical and Biological Sensors ad Analytical Methods II), pp. 49-57.*

* cited by examiner

*Primary Examiner*—Alex Noguerola
(74) *Attorney, Agent, or Firm*—Nixon & Vanderhye P.C.

(57) ABSTRACT

A polymer based enzyme electrode useful for estimation for cholesterol is disclosed. The electrode has an ion-doped layer to increase the conductivity of the poly pyrrole layer. The ion doping is achieved by incorporating dodecyl benzene sulphonate (DBS) in the poly pyrrole film deposited by electrochemical deposition The enhanced conductivity due to ion doping helps in faster estimation of cholesterol having a measured response time of 30 seconds. The shelf life of the electrode is at least eight weeks without a mediator at room temperature.

17 Claims, 2 Drawing Sheets

POLYMER BASED ENZYME ELECTRODE FOR ESTIMATION OF CHOLESTEROL AND PROCESS FOR PREPARATION THEREOF

FIELD OF THE INVENTION

The present invention relates to a polymer based enzyme electrode for estimation of cholesterol and a process for the preparation thereof. More particularly, the present invention relates to a novel enzyme electrode coated with a film of dodecylbenzene sulfonate ion-doped polypyrrole film containing immobilized cholesterol oxidase therein. The present invention also provides a process for the preparation of an enzyme electrode by coating an immobilized cholesterol oxidase (ChOx) dodecylbenzene sulfonate ion doped polypyrrole film on a conducting substrate.

BACKGROUND OF THE INVENTION

Cholesterol and its fatty acid esters are important compounds for human beings since they are components of nerve and brain cells and are precursors of other biological materials, such as bile acid and steroid hormones. [P. L. Yeagle, Biology of Cholesterol (CRC Press): Its function and metabolism in biology and medicine: (Plenum: New York, 1972)]. Cholesterol determination in blood is clinically important for the diagnosis of heart diseases since accumulation of cholesterol and its fatty acid esters in blood due to excessive ingestion can be fatal (D. Noble Anal. Chem., 1993, vol 65, pp1037A–41A). The normal range of blood serum values extends from 3 to 6 mM for total cholesterol while in the hyperlipidamic condition the level can increase to 10 mM.

It is therefore desired to develop techniques that allow convenient and rapid determination of cholesterol. Various methods have been employed in the art for stabilization and immobilization of enzymes within carbon paste or covalently linking it to the surface of glassy carbon electrode or immobilizing it within a polymer film for the preparation of enzyme electrode.

Methods of immobilization of biorecognition elements have been reported for use in chemical sensing [R. F. Taylor, Protein Immobilizing Fundamentals and Applications: Marcel Dicker, New York (1975) Chapter 8, 263–303 and H. H. Weetall, Immobilized Enzyme; Antigen, Antibodies and Peptides Preparation and Characterization; Marcel Dicker, New York (1975) Chapter 6, 263–303]. The methods reported in literature can generally be classified into one of the following categories (1) physiorption (2) covalent attachment or (3) entrapment, among which physisorption is the simplest immobilization approach.

Several disadvantages arise with these methods of immobilization such as problems associated with the large size of the biorecognition elements (e.g. proteins and enzymes). Physisorption produces a range of biorecognition element orientations and apparent biding affinities. Besides physisorption generally leads to a population of biorecognizing elements that is completely unresponsive to target analyte. The immobilized species is completely unresponsive to target analyte. The immobilized species will often leach/desorb from sensing interface because there are no covalent bonds. Covalent schemes generally lead to more stable and uniform (interim of biorecognition orientation) interface and enzyme leaching is minimized. Unfortunately covalent attachment involves one or more chemical transformation and tends to be time consuming and expensive.

Electrochemically polymerised conducting polymers have also received considerable attention over the last two decades. The remarkable switching capacity of these materials between the conducting oxidised (doped) and he insulating reduced (undoped0 state is the basis of many applications. For example, polyconjugated conducting polymers have been proposed for biosensing applications because of advantageous characteristics such as direct and easy deposition on the sensor electrode by electrochemical oxidation of monomer, control of thickness by deposition of charge and redox conductivity and polyelectrolyte characteristics of the polymer useful for sensor applications.

Polypyrrole is commonly used for these applications since it meets with the above stated requirements. Polypyrrole has several advantageous properties such as easy water solubility, easily oxidisable, low cost of monomer, and the high chemical stability of the polymer [Diaz et al, J. Electroanal Chem 1981, 129, 115].

Yabuki et al [J. Chem. Soc. Commun, 1989, 41, 945] report an electrochemically synthesised polypyrrole membrane with the electropolymerised polypyrrole working as an efficient molecular interface for electron transfer. The result polypyrrole (PPY) polymer was clarified with a flavin adenine dinucleotide (FAD) entrapped PPY membrane with a smooth and reversible oxidation and reduction of FAD, the prosthetic group of glucose oxidase. Yabuki et al [J. Electroanal Chem, 1990, 277, 179] also report the use of nicotinamide adenine dinucleotide in a mediator-entrapped polymer membrane electrode.

It is known in the art that the conductivity of polypyrrole deposited, for example on textile, from an aqueous solution of polypyrrole undergoing oxidative polymerisation depends of the dopant anion such as anthraquinone-2-sulfonic acid which gives the least surface resistance [Theibelmont et al, Polym Degrad Stab 1994, 43, 293; Kuhn et al, Synth Metab, 1993, 55, 3707; Gregory et al, Synth Metab, 1989, 28, 823]. The redox species such as phenazene, thionine and ferricyanide allow accurate electrochemical determination of cholesterol without any interference of several dissolved compounds in blood such as ascorbic acid or uric acids.

It is therefore highly desirable to develop biosensors that allow conventional and rapid determination of cholesterol.

OBJECTS OF THE INVENTION

The main object of the present invention is to provide a polymer based enzyme electrode for estimation of cholesterol Another object of the present invention is to provide a process for the preparation of a enzyme electrode that provides an accurate measurement of cholesterol in solution.

Yet another object of the present invention is to provide an enzymatic stable, cost-effective high sensitive enzyme electrode.

Still another object of the present invention is to provide an enzyme electrode, which provides an accurate measurement of cholesterol within a short time period.

SUMMARY OF THE INVENTION

Accordingly the present invention provides a novel polymer based enzyme electrode for estimation of cholesterol comprising:
  i. an electrically conducting substrate,
  ii. ion doped polypyrrole film provided on the conducting substrate, iii. physically immobilized cholesterol oxidase with a mediator provided on the doped polypyrrole film.

In one embodiment of the invention, the electrically conducting substrate comprises a coated glass plate.

In another embodiment of the invention the conducting glass plate used is an indium tin oxide coated glass plate.

In another embodiment of the invention the ion doped polypyrrole film comprises a dodecylbenzenesulphonate doped polypyrrole film.

In still another embodiment of the invention the concentration of dodecylbenzene sulphonate in the polypyrrole film is 1:1 (v/v).

In a further embodiment of the invention the mediator used is potassium ferricyanide.

In a still further embodiment of the invention the strength of cholesterol oxidase is in the range of 3–5 IU per square centimeter of polypyrrole film.

In an embodiment of the invention the enzyme electrode has a sensitivity of about 0.4 volt, a response time of about 30 seconds, a working range of 6.5–7.2 pH and a shelf life of at least 8 weeks at a temperature in the range of 20–25° C.

In another embodiment of the invention the enzyme electrode is useful for the estimation of cholestrol in the presence of glucose and ascorbic acid.

The present invention also provides a process for preparing a polymer based enzyme electrode useful for estimation of cholesterol in aqueous medium, comprising the steps of:
a. cleaning an electrically conducting substrate by conventional methods
b. mixing dodecylbenzene sulphonate (DBS) with pyrrole in a ratio of 1:1 v/v,
c. electrochemically depositing DBS and pyrrole film on the clean electrically conducting substrate, to obtain a electrically conducting substrate with DBS doped polypyrrole film deposited thereon,
d. depositing physically immobilized cholesterol oxidase from a solution consisting of cholesterol oxidase and a mediator in a buffer on the DBS doped polypyrrole deposited conducting substrate obtained in step c,
e. drying the coated conducting substrate of step d).

In one embodiment of the invention, the electrically conducting substrate comprises of a coated glass plate.

In another embodiment of the invention the coated conducting glass plate used comprises an indium tin oxide coated glass plate.

In one embodiment of the invention, the step of drying is done at a temperature of 20–25° C. for a period of about 12 hrs In an embodiment of the invention the strength of DBS used is 0.05–0.15 M.

In still another embodiment of the invention the current used in the electrochemical deposition is about 2 mA.

In a further embodiment of the invention the reference electrode used in electrochemical deposition is made of platinum.

In another embodiment of the invention mediator used is potassium ferricyanide.

In another embodiment of the invention the strength of cholesterol oxidase used is in the range of 3–5 IU per square centimeter of polypyrrole film.

In still another embodiment of the invention, the buffer used is a phosphate buffer with a pH in a range of 6.5–7.2.

BRIEF DESCRIPTION OF THE ACCOMPANYING DRAWINGS

DETAILED DESCRIPTION OF THE INVENTION

An indium tin oxide coated glass substrate was taken and cleaned thoroughly by conventional chemical means. Pyrrole monomer as obtained from the supplier was first purified by fractional distillation at 130° C. and stored at 4° C. till required for use. Dodecyl benzene sulphonate (DBS) and distilled pyrrole were taken in a ratio of 1:1 (v/v) and mixed thoroughly for electrochemical deposition. Standard electrochemical Interface (Model SI 1286) was used to deposit films of DBS/Pyrrole was used. The deposition conditions used were 2 mA current for a period of about 1 minute. This gave a film of doped polypyrrole film with the dopant agent being DBS, the reference electrode being platinum.

Onto the doped polypyrrole film obtained above, immobilised enzyme cholesterol oxidase was physically deposited. To achieve this a solution of 10 µL of a solution of 0.1M phosphate buffer was prepared with that of 3 IU of cholesterol oxidase and 0.1M of potassium fericyanide. This solution was then spread over the DBS PPY film of area 1 cm$^2$. The resulting film was dried at room temperature for about 12 hours and kept in refrigerated condition till further use. The resulting structure has the form ChOx/Fe$^{3+}$/DBS-PPY and is ready for use in cholesterol estimation.

A standard cholesterol solution was prepared by dissolving 3 mg of cholesterol in 12.8 ml of propan-2-ol and was mixed with 5.85 ml of Triton X-100 surfactant. After homogenization the volume was made up to 100 ml with 0.1M phosphate buffer (pH 7.0) and thermostat at 35° C. This standard solution was further diluted with water to make different cholesterol solutions.

Figure 1:
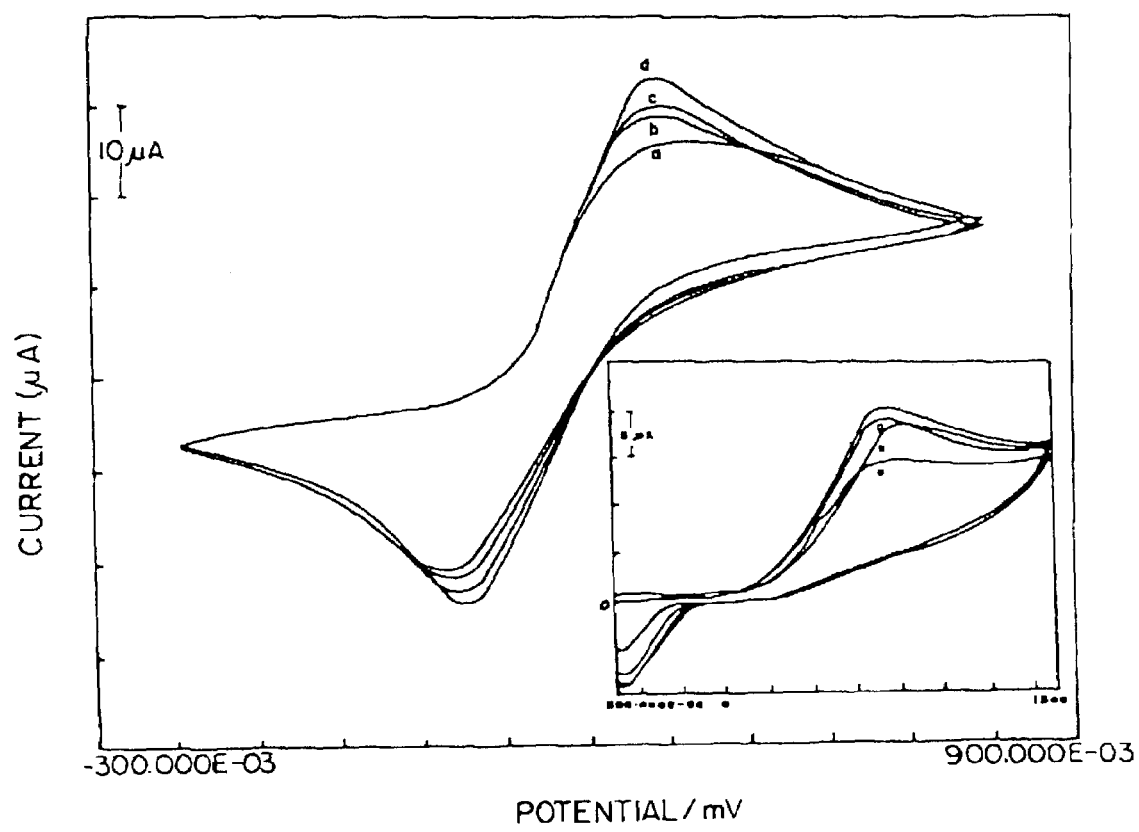
FIG. 1 shows the electrochemical studies of DBS-Poly pyrrole film containing immobilized cholesterol oxidase and potassium ferricyanide.

The FTIR spectra of electrochemically prepared ChOx/DBS-PPY film revealed sharp peaks at 1500–1400 cm$^{-1}$ and 1100–1000 cm$^{-1}$ These may be attributed to C=C stretching mode and C—C stretching respectively. The characteristic peaks at 3100 and 3500 cm-$^1$ assigned to N—H linkage and N—H stretching of free amide indicate the presence of immobilized cholesterol oxidase (ChOx). The entrapment of enzyme (ChOx) is also confirmed with the help of UV-Visible spectroscopy. When the ChOx/DBS/PPY film is immersed in phosphate buffer containing cholesterol, the observed increase in absorbance at 240 nm is characteristic of cholestenone produced by enzymatic solution. The results indicate that the ChOx has been incorporated in the DBS-ion doped PPY film. ChOx/DBS-PPY/ITO films are also studied for the stability at both 25° C. and 4° C. in refrigerated condition. The film is stable for 12 weeks when stored at 4–5° C. in refrigerated conditions. However, the film is stable for 8 weeks at 25–35° C. FIG. 1 shows amperometric response studies of polymeric modified enzyme electrode. It shows linearity up 8 mM of cholesterol concentration Linearity is attributable to the presence of dodecylbenzenesulphonic acid ions Linearity in response is required to measure the metabolite concentration in solution precisely The polymer based enzyme electrode of the invention has a very fast response time of 30 seconds and having a long shelf life of at least 8 weeks at room temperature a particular feature of the invention is that the immobilization of the enzyme cholesterol oxidase (ChOx) is done on an electrochemically prepared dodecylbenzene sulfonate ion doped polypyrrole film onto a conducting indium tin oxide (ITO) coated glass plate.

The following examples are given by the way of illustration and therefore should not be construed as limiting limit the scope of the present invention in any manner.

EXAMPLE I (i) Preparation of Dodecylbenzene Sulfonate Ion Doped Polypyrrole Film Dodecyl benzene sulfonate ion doped polypyrrole film was electrochemically prepared on indium tin oxide (ITO) glass plate by taking 0.1M monomer and 0.1M dodecyl benzene sulfonate in a ratio of 1:1 (v/v) in an aqueous medium and passing a constant current of 2 mA through the solution, using platinum as the reference electrode. The films thus prepared were then washed with double distilled deionised water prior to being used. Prior to film casting indium tin oxide (ITO) coated glass plates were first treated with $HNO_3$, for about 2 hrs and were subsequently rinsed thrice with Millipore water. The glass slides were finally washed with n-propanol prior to film coating technique.

(ii) Immobilization of Enzyme and a Mediator in Film

For the immobilization of cholesterol oxidase (ChOx) 10 µl of a solution of 0.1M phosphate buffer (pH 7.0) containing 3 IU of ChOx (18 units per mg solids, 5 mg/0.3 mL) and 5 µl of 0.1M potassium ferricyanide were physically deposited on to a 1×1 $cm^2$ DBS-PPY film. The films thus obtained were dried at room temperature for about 12 hours and were stored at a temperature of about 4° C.

(iii) Preparation of Cholesterol Solution

The cholesterol (3.86 mg) was dissolved in 12.8 ml of propan-2-ol and was mixed with 3.85 ml of Triton X-100 surfactant. After homogenization the volume was made up to 100 ml with 0.1M phosphate buffer (pH 7.0) and thermostat at 35° C. This standard solution was further diluted with water to make different cholesterol solutions.

(iv) Enzyme Activity Measurements

A solution of 0.05 $cm^3$ of 6 mm cholesterol dissolved in 2-propanol and of 3 $cm^3$ of 0.1 M phosphate buffer (pH 7.0) were mixed and kept in a thermostat at 35° C. The ChOx immobilized DBS-PPY film coated glass plates were immersed in the presence of horse radish peroxidase and incubated for about 2 minutes. The coated ITO glass plate was immersed and incubated for 2 minute, the plate was removed and the absorbance of the solution was measured at 240 nm using a double beam spectrometer to determine the cholesterol produced by the enzymatic reaction. The apparent enzyme activity ($Ucm^3$) was evaluated by the following procedure based on the difference in absorbance before and after incubation of the enzyme immobilized sol-gel glass plate.

$$(U\ cm^{-2}) = AV/\epsilon ts$$

Where A is the difference in absorbance before and after incubation, V is the total volume (3.05 $cm^3$), $\epsilon$ is the milli molar extinction coefficient of cholesterol (12.2), t is the reaction time (min) and s is the surface area (1×1 $cm^2$) of film. One unit of enzyme activity ($U\ cm^{-2}$) is defined as the activity that results in the production of 1 µmol of cholestenone per minute. The enzyme activity measurements were made on the enzyme ChOx immobilized DBS doped PPY film.

The immobilized enzyme stability of the electrode (ChOx/$Fe^{3+}$/DBS-PPY) was studied at both 25° C. and at 4° C. in refrigerated condition. The enzyme electrode film was found to stable for 12 weeks when stored at 4° C. in refrigerated condition. At 25° C. the enzyme electrode was stable for 8 weeks.

EXAMPLE II

Electrochemical Studies of DBS-Poly Pyrrole Film Containing Immobilized Cholesterol Oxidase and Potassium Ferricyanide.

Cyclicvoltammtry experiments was performed in 0.1M phosphate buffer (pH 7.0) using enzyme (ChOx) immobilized DBS-PPY/ITO film with ferricyanide ion mediator as working electrode, Ag/AgCl as reference electrode and platinum (pt) wire as a counter electrode. The reaction scheme is as follows:

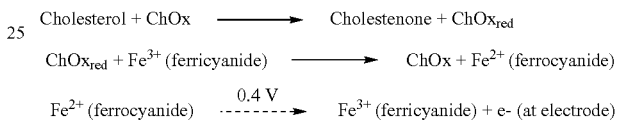

The oxidation current is recorded as the sensor (enzyme electrode) response in the amperometric biosensor. Owing to the direct immobilization of the enzyme, the sensor properties such as time and sensitivity are the reflection of the immobilized enzyme.

An oxidation peak was observed at 0.4 V versus Ag/AgCl, which increases with an increase in cholesterol concentration (2 to 10 mM), as shown in FIG. 1.

EXAMPLE III

Amperometric Response Studies

Figure 2:
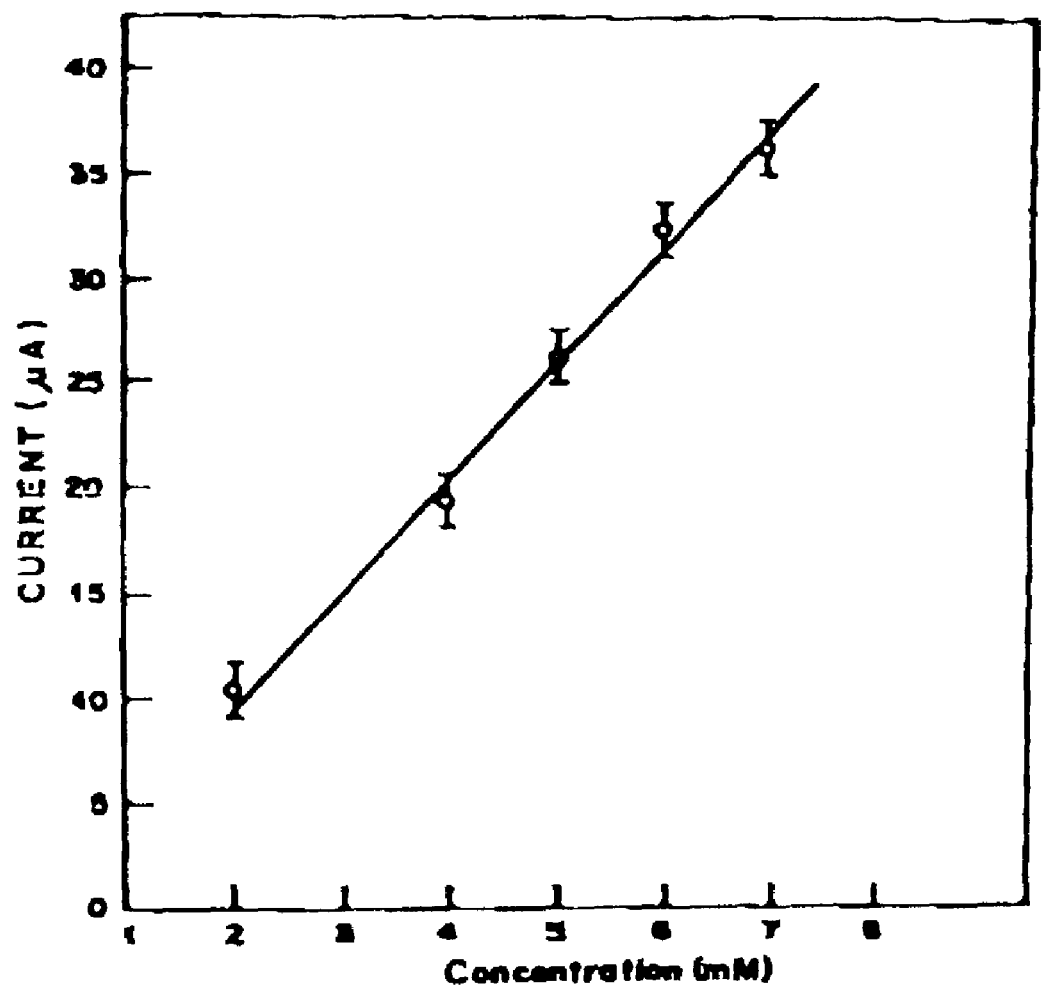
FIG. 2 shows the amperometric response studies carried out for the amperometric determination of cholesterol in phosphate buffer (pH 7.0).

A three electrode cell configuration similar to the one used in cyclic voltammeteric experiment was used for the amperometric determination of cholesterol in phosphate buffer (pH 7.0). The results are shown in FIG. 2. The working electrode having potassium ferricyanide as mediator (ChOx/$Fe^{3+}$/DBS-PPY) was polarizing at 0.4V with respect to Ag/AgCl electrode. The anodic current measured in 6 mM cholesterol solution (1 mL) at ChOx/$Fe^{3+}$/DBS-PPY/ITO electrode polarized at 0.4V yield the state in a time period of 30 second. This fast response of ChOx/$Fe^{3+}$/DBS-PPY/ITO electrode to cholesterol solution reveals a fast electronic exchange that occurs ChOx and potassium ferricyanide mediator.

The Main Advantages of the Present Invention Are:
1. The enzyme electrode prepared shows fast response to cholesterol in solution
2. The enzyme electrode prepared is shelf stable for a longer time.
3. The enzyme electrode prepared is highly sensitive to cholesterol.

We claim:

1. A polymer based enzyme electrode for estimation of cholesterol comprising:

i. an electrically conducting substrate comprising an indium tin oxide coated glass plate, ii. an ion doped polypyrrole film provided on said electrically conducting substrate, iii. physically immobilized cholesterol oxidase with a potassium ferricyanide mediator provided on the doped polypyrrole film coated conducting substrate wherein the ion doped polypyrrole film comprises dodecylbenzene sulphonate doped polypyrrole film, to provide an ITO/DBS-PPY/ChOx/Fe3+ electrode configuration.

2. An enzyme electrode as in claim 1 wherein the concentration of dodecylbenzene sulphonate in the polypyrrole film is 1:1 v/v.

3. An enzyme electrode as in claim 1 wherein the strength of cholesterol oxidase is in the range of 3–5 IU per square centimeter of polypyrrole film.

4. An enzyme electrode as in claim 1 wherein the enzyme electrode has a sensitivity of about 0.4 volt.

5. An enzyme electrode as in claim 1 wherein the enzyme electrode has a response time of about 30 seconds.

6. An enzyme electrode as in claim 1 wherein the enzyme electrode has a working range of 6.5–7.2 pH.

7. An enzyme electrode as in claim 1 wherein the enzyme electrode has a shelf life of at least 8 weeks at a temperature in the range of 20–25° C.

8. A process for the preparation of a polymer based enzyme electrode useful for estimation of cholesterol in aqueous medium, which comprises the steps of:

a. cleaning an electrically conducting substrate of indium tin oxide coated on a glass plate by conventional methods;

b. mixing dodecylbenzene sulphonate (DBS) with pyrrole in a ratio of 1:1 v/v, c. electrochemically depositing DBS and pyrrole film on the clean electrically conducting substrate to obtain a DBS doped polypyrrole deposited electrically conducting substrate, d. physically depositing cholesterol oxidase from a solution consisting of cholesterol oxidase and a potassium ferricynanide mediator in a buffer on the DBS doped polypyrrole deposited conducting substrate obtained in step c, e. drying the coated conducting substrate of step d to provide an ITO/DBS-PPY/ChOx/Fe3+ electrode configuration.

9. A process as in claim 8 wherein the drying is done at a temperature in the range of 20–25° C. for a period of about 12 hrs.

10. A process as in claim 8 wherein the strength of DBS used is in the range of 0.05 to 0.15M.

11. A process as in claim 8 wherein the electrochemical deposition is carried out using a current of about 2 mA and a reference electrode.

12. A process as in claim 11 wherein the reference electrode is a platinum electrode.

13. A process as in claim 8 wherein the strength of cholesterol oxidase is in a range of 3–5 IU.

14. A process as 8 wherein the buffer used is a phosphate buffer used with a pH in the range of 6.5–7.2.

15. A polymer based enzyme electrode for estimation of cholesterol with a sensitivity of about 0.4 volt, a response time of about 30 seconds, a working range of 6.5–7.2 pH and a shelf life of at least 8 weeks at a temperature in the range of 20–25° C., the polymer based enzyme electrode comprising:

i. an electrically conducting substrate comprising indium tin oxide coated on a glass plate, ii. ion doped polypyrrole film provided on said electrically conducting substrate, iii. physically immobilized cholesterol oxidase with a mediator of potassium ferricyanide provided on the doped polypyrrole film coated conducting substrate wherein the ion doped polypyrrole film comprises dodecylbenzene sulphonate doped polypyrrole film to provide an ITO/DBS-PPY/ChOx/Fe3+ electrode configuration.

16. An enzyme electrode as in claim 15 wherein the concentration of dodecylbenzene sulphonate in the polypyrrole film is 1:1 v/v.

17. An enzyme electrode as in claim 15 wherein the strength of cholesterol oxidase is in the range of 3–5 IU per square centimeter of polypyrrole film.

* * * * *